(12) United States Patent
Rowley

(10) Patent No.: US 12,194,160 B2
(45) Date of Patent: Jan. 14, 2025

(54) TRANSDERMAL PATCH PROVIDING IMPROVED PERMEABILITY AND COMPOSITION

(71) Applicant: HydraPatch Inc., North Brunswick, NJ (US)

(72) Inventor: Clifford Rowley, North Brunswick, NJ (US)

(73) Assignee: HydraPatch Inc., North Brunswick, NJ (US)

( * ) Notice: Subject to any disclaimer, the term of this patent is extended or adjusted under 35 U.S.C. 154(b) by 64 days.

(21) Appl. No.: 17/646,009

(22) Filed: Dec. 27, 2021

(65) Prior Publication Data

US 2022/0117907 A1 Apr. 21, 2022

Related U.S. Application Data

(63) Continuation of application No. 16/918,252, filed on Jul. 1, 2020.

(Continued)

(51) Int. Cl.
*A61K 9/70* (2006.01)
*A61K 31/19* (2006.01)

(Continued)

(52) U.S. Cl.
CPC .......... *A61K 9/7038* (2013.01); *A61K 9/7053* (2013.01); *A61K 9/7061* (2013.01); *A61K 9/7069* (2013.01); *A61K 9/7076* (2013.01); *A61K 31/19* (2013.01); *A61K 31/191* (2013.01); *A61K 33/00* (2013.01); *A61K 33/06* (2013.01);

(Continued)

(58) Field of Classification Search
CPC .. A61K 9/7023; A61K 9/7038; A61K 9/7053; A61K 9/7061; A61K 9/7069; A61K 9/7076; A61K 31/19; A61K 31/191; A61K 33/00; A61K 33/06; A61K 33/42; A61L 2300/00; A61M 37/00; A61M 2037/0007; A61M 37/0015; A61M 2037/0023
See application file for complete search history.

(56) References Cited

U.S. PATENT DOCUMENTS 5,683,712 A 11/1997 Cavazza
2004/0137040 A1* 7/2004 Nogami ............... A61K 9/0053
424/443

(Continued)

FOREIGN PATENT DOCUMENTS

WO WO9112734 * 9/1991 ............... A23L 2/38

*Primary Examiner* — Lauren P Farrar
(74) *Attorney, Agent, or Firm* — Robert E. Colletti; Haug Partners LLP

(57) ABSTRACT

A transdermal patch contains a water-based solution containing electrolytes, vitamins, and at least one permeation enhancer. The water-based solution also acts as an adhesive matrix which binds the patch together. The solution is transferred to the body via an embossed release liner. In use, the permeation of electrolytes into the bloodstream improves the body's ability to manage hydration. The permeation enhancer increases the porosity of the skin in contact with the transdermal patch to make possible the permeation of the solution into the body. Critical proportions of solvent, solutes, and permeation enhancers are disclosed which have been found to make permeation of otherwise non-absorbable ingredients possible.

21 Claims, 4 Drawing Sheets

Related U.S. Application Data

(60) Provisional application No. 62/869,944, filed on Jul. 2, 2019.

(51) Int. Cl.
*A61K 31/191* (2006.01)
*A61K 33/00* (2006.01)
*A61K 33/06* (2006.01)
*A61K 33/42* (2006.01)
*A61M 37/00* (2006.01)

(52) U.S. Cl.
CPC ......... *A61K 33/42* (2013.01); *A61M 37/0015* (2013.01); *A61M 2037/0023* (2013.01)

(56) References Cited

U.S. PATENT DOCUMENTS

| | | |
|---|---|---|
| 2005/0249793 A1 | 11/2005 | Blitzer et al. |
| 2005/0287195 A1* | 12/2005 | Solomon ............... A61K 9/0014 424/449 |
| 2006/0029673 A1* | 2/2006 | Breitenbach ............ A61P 13/00 424/486 |
| 2007/0077287 A1* | 4/2007 | Goodrich ............... A61K 9/703 424/449 |
| 2008/0254107 A1* | 10/2008 | Jacques ................ A61K 9/7023 514/60 |
| 2008/0294116 A1* | 11/2008 | Wolter ................. A61K 9/0021 604/173 |
| 2009/0221985 A1 | 9/2009 | Bukshpan et al. |
| 2012/0265158 A1 | 10/2012 | Braun et al. |
| 2018/0296497 A1* | 10/2018 | Schepis ................ A61K 31/045 |
| 2018/0311363 A1* | 11/2018 | Takita ................. A61K 31/135 |
| 2018/0318341 A1* | 11/2018 | Kuefner ............... A61K 9/0021 |
| 2020/0085760 A1* | 3/2020 | Haba Cardo ........ A61K 31/197 |

* cited by examiner

TRANSDERMAL PATCH PROVIDING IMPROVED PERMEABILITY AND COMPOSITION

CROSS-REFERENCE TO RELATED APPLICATION(S)

The present application is a continuation of U.S. patent application Ser. No. 16/918,252 filed Jul. 1, 2020, which claims the benefit under 35 U.S.C. § 119 (e) of U.S. Provisional Patent Application No. 62/869,944 filed Jul. 2, 2019. All prior applications are herein incorporated by reference in their entirety.

TECHNICAL FIELD

The present invention relates generally to the field of medical devices of existing art and more specifically relates to a transdermal hydration patch.

BACKGROUND

The following includes information that may be useful in understanding the present disclosure. It is not an admission that any of the information provided herein is prior art nor material to the presently described or claimed inventions, nor that any publication or document that is specifically or implicitly referenced is prior art.

Dehydration is a global health threat. Dehydration can reduce physical and mental performance, cause lack of focus, headaches, constipation, lethargy, and in extreme cases, death. While dehydration can be caused simply by lack of water intake, it can also be caused or exacerbated by poor water management when internal levels of vitamins and minerals prevent the body from properly managing water usage. Some commentators believe that up to 245 million Americans may suffer from dehydration.

It is known in the art to absorb ingredients into the human body by applying patches to the skin in order to transfer the ingredients directly to the bloodstream through skin permeation. Such devices are known in the art as transdermal patches. Advantages of such methods of intaking ingredients include ease of use, disposability of the carrying medium, and the avoidance of digestive side effects (i.e. nausea). It has been known in the art to use transdermal patches to intake substances such as nicotine and amino acids. While existing transdermal patches have been of use in certain applications (i.e. nicotine patches for reducing dependence on smoking, birth control patches, and Vitamin B patches), there are many potential health applications to which transdermal patches have not yet been applied. One such potential application is hydration.

A primary limitation of absorbing substances transdermally using such patches is that the human skin is relatively impermeable to many substances that would be desirable for such an application. For example, the skin may readily absorb lipids, but not water or electrolytes. This property of skin makes absorbing water-soluble substances through the skin impractical. While many non-proven health products on the market claim to allow permeation of vitamins, minerals, and other substances through the skin, it is perceived that the efficacy of these products are suboptimal lacking a novel permeation solution. A suitable solution is desired.

In the relevant art, U.S. Pat. No. 5,683,712 to Paolo Cavazza relates to a transdermal patch for the administration of homeopathic drugs. The described transdermal patch includes a medical device for the administration of active ingredients or drugs at very low doses, and particularly of homeopathic drugs, comprising a transdermal patch with a support membrane, a layer of porous adhesive, a microporous membrane and a gel containing the homeopathic drug to be administered. Cavazza attempts to overcome problems associated with alternative modes of drug administration (i.e. oral). Nonetheless, Cavazza's solution maintains the same aforementioned problems, and does not provide a suitable solution for transdermally conveying difficult-to-absorb solutes.

SUMMARY

In view of the foregoing disadvantages inherent in the known transdermal patch art, the present disclosure provides a novel transdermal patch having improved permeability and a hydrating composition, and a combination over-the-counter external analgesic drug and cosmetic.

The disclosed transdermal patch having improved permeability and composition provides a novel solution to the transdermal permeation problem, being able to effectively enact permeation of vitamins, and electrolytes through the skin and enable the body to maintain improved hydration levels.

A primary objective of the disclosed transdermal patch is to enact effective hydration of a user by supplying the body with electrolytes and vitamins enabling the body to better self-regulate hydration. Another objective is to provide a patch with the disclosed applications which is also an over-the-counter medication. Yet another application is to provide a patch which is able to contain a "heavier" or denser composition in the patch and still be able to convey the contents to the body through the skin of the user.

The transdermal patch contains a water-based solution containing electrolytes, vitamins, and at least one permeation enhancer. The water-based solution further acts as a structural element of the patch, being an adhesive matrix which binds the patch together. In use, the solution is transferred to the body via an embossed release liner placed in contact with the skin. The permeation of electrolytes into the bloodstream improves the body's ability to manage hydration. The permeation enhancer increases the porosity of the skin in contact with the transdermal patch to make possible the passage of the solution into the body. Critical proportions of solvent, solutes, and permeation enhancers are disclosed which have been found to make permeation of otherwise non-absorbable ingredients possible.

In one embodiment of the transdermal patch, the embossed release liner and the adhesive matrix may be of a smaller area coverage than the liner. The excess liner space that does not overlap with the release liner may circumscribe the release liner, and may be coated with a solvent-based adhesive which adheres to the skin around the release liner to adhere the transdermal patch to the skin of the user. The liner may include a water-proof liner layer, preferably composed of a polymer. The polymer may be flexible and suitable for printing graphics on the liner. The adhesive may be an occlusive compound activatable by body heat and skin moisture. The adhesive may not melt or disperse when wetted. In this format, the adhesive matrix may be divided between forty-percent of active formula and sixty-percent adhesive.

For purposes of summarizing the invention, certain aspects, advantages, and novel features of the invention have been described herein. It is to be understood that not necessarily all such advantages may be achieved in accordance with any one particular embodiment of the invention.

Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and methods of use for the present disclosure, a transdermal patch having improved permeability and composition, constructed and operative according to the teachings of the present disclosure.

The various embodiments of the present invention will hereinafter be described in conjunction with the appended drawings, wherein like designations denote like elements.

DETAILED DESCRIPTION

Figure 1:
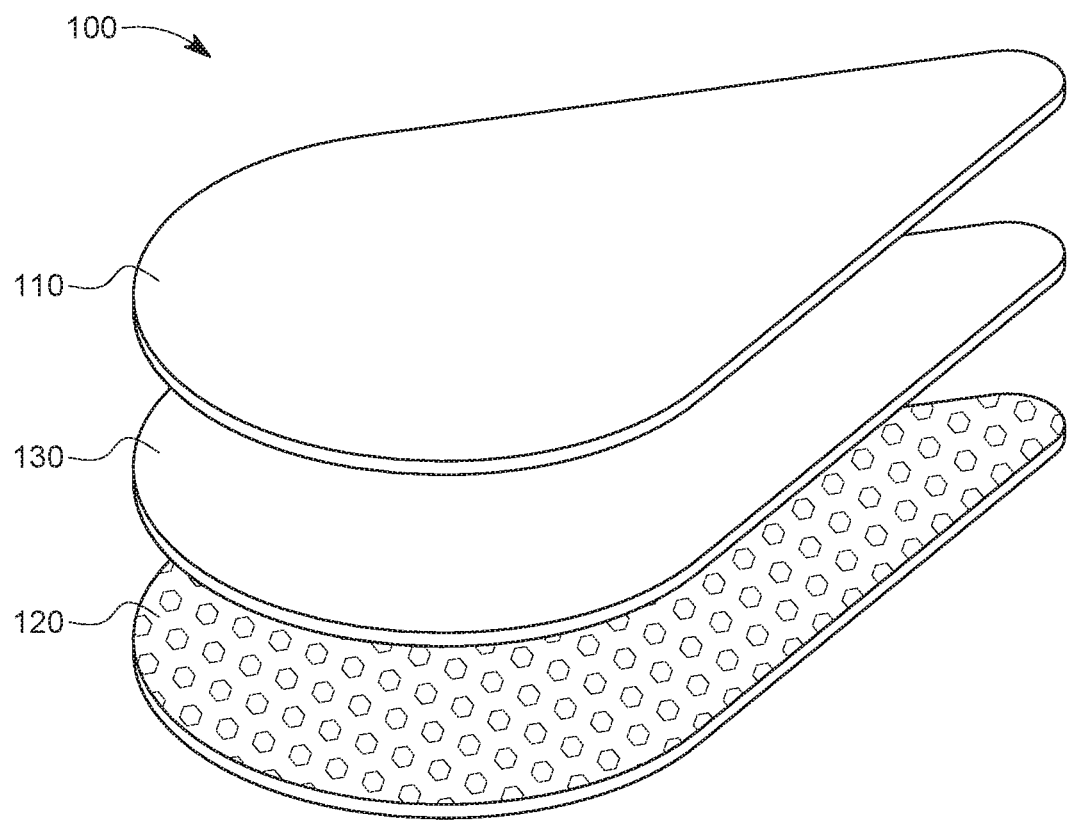
FIG. 1 is an exploded view of the transdermal patch illustrating the laminated construction of the patch according to an embodiment of the disclosure.

As discussed above, embodiments of the present disclosure relate to a medical device and more particularly to a transdermal patch having improved permeability and composition as used to improve the hydration of the body by conveying electrolytes to the body via transdermal permeation.

The present transdermal patch presents a new method of hydrating the body by enacting permeation of critical electrolytes and vitamins. Such a product is lacking in the prior art; so much so that NSF International (i.e. National Sanitation Foundation) currently lacks a testing procedure for such a product.

The transdermal patch implements a unique structure and formulation to provide electrolytes and nutrients to maintain hydration and prevent dehydration of the body. Dehydration is a widespread health factor that affects most people. Dehydration is also linked to stress. These undesirable factors may be eliminated by proper hydration through use of the patch. Use of the transdermal patch may further act to improve overall mental and physical performance by stabilizing hydration levels over time. As such, use of the patch may benefit the general populous, not only those working as first responders, military personnel, surgical staff, E-Sport gamers, and others engaged in demanding physical activity for extended time periods where proper hydration is made difficult by obvious time and focus demands of the job, but almost anyone engaged in physical activity. Other users who may benefit from this hydration aid include truck drivers, aircraft pilots, construction trades, factory workers, teachers, and office staff. In use, the patch acts to stabilize hydration levels between taking liquids. For individuals who must bear equipment during work, the weight of liquids carried can be reduced. Also, for those training or performing physically for prolonged periods, any number of physical performance related activities can be enhanced with proper hydration. Additionally, use of the transdermal patch to improve hydration can reduce waste caused by the disposal of excessive water containers (i.e. plastic bottles, aluminum cans, etc.) when users consume excessive water due to poor internal hydration management.

The delivery of electrolytes and nutrients using a patch offers advantages over traditional delivery methods. The patch reduces the amount of time spent drinking liquids and stopping to urinate. The delivery of electrolytes and nutrients does not require digestion and the resultant loss of nutrients and energy expended in the digestion process and the nutrients are released over a period of time. The delivery of hydration by transdermal patch also minimizes the psychological effect of feeling "heavy" or "full" as occurs drinking fluids traditionally. The patch consists of a transdermal patch with adhesive for applying on the skin, permeability enhancers and the nutrients. The outer surface of the patch provides area for branding, design or promotion.

Referring now more specifically to the drawings by numerals of reference, there is shown in FIGS. 1-4, various views of a transdermal patch 100.

FIG. 1 shows a transdermal patch during an 'in-use' condition, according to an embodiment of the present disclosure. Here, the transdermal patch may be beneficial for use by a user to improve the hydration of the body by delivering electrolytes to the body via transdermal permeation. As illustrated, the transdermal patch 100 may include backer 110, embossed release liner 120, and adhesive matrix 130. Adhesive matrix 130 binds backer 110 to embossed release liner 120. In use, embossed release liner 120 is placed in direct contact with the skin of the user, and adhesive matrix 130, as it begins to absorb through embossed release liner 120 into the skin, helps adhere embossed release liner 120 to the skin. Adhesive matrix 130 may contain water (as a solvent), electrolytes, vitamins, an adhesive agent, and a permeation enhancer. The permeation enhancer may increase the permeability of adhesive matrix 130 into the skin. The permeation enhancer may include menthol. In some embodiments, menthol may be supplemented by additional permeation enhancers, such as dimethyl sulfoxide (DMSO). The permeation enhancer may comprise peppermint oil. Adhesive agent 130 may include one or more of sodium polyacrylate, polyacrylic acid, carboxymethyl cellulose, and povidone. Polysorbate 80 may be contained within adhesive matrix 130, acting as a surfactant and emulsifier. In an exemplary embodiment, adhesive matrix 130 may contain between ten and thirty percent water. It has been found that this range of water content in the final product is sufficient to enable retention of the necessary solutes, but also low enough to maintain the structural integrity of the adhesive matrix 130 and bind the embossed release liner 120 to backer 110. During manufacture, the initial composition may contain as much as ninety percent water to absorb the solutes, before being dried and compressed into the final product that constitutes adhesive matrix 130. Since an initial composition of ten to thirty percent water would not be sufficient to absorb all solutes within the water, the drying process is necessary to initially create a homogenous solution before water content is decreased and the resulting adhesive matrix 130 is formed.

As illustrated, transdermal patch 100 may have a perimeter in the form of a water-drop shape.

The active ingredient (i.e. active ingredient under FDA classification) of transdermal patch 100 is menthol. Menthol is the primary ingredient as an external analgesic which also increases permeability of the formula contained within adhesive matrix 130. Of the final weight of the patch, menthol may make up 0.01 to 16 percent. An exemplary proportion may be approximately 0.011 percent by weight. An ideal mass of menthol may be between 30 and 35 milligrams in an exemplary embodiment. The total mass of the final patch may range from 0.05 to 0.15 ounces. In use, transdermal patch 100 may convey contents to the bloodstream for approximately eight hours. The estimated shelf life of the product is two years.

In an exemplary embodiment, adhesive matrix 130 may further include an anti-inflammatory. While dimethyl sulfoxide and menthol may in and of themselves act as anti-inflammatories, additional ingredients acting as dedicated anti-inflammatories may be added. For the purposes of this specification, "anti-inflammatory" is used to mean any medication, compound, or ingredient recognized by the FDA as useful for anti-inflammatory purposes. Yet further, adhesive matrix 130 may include amino acids. Leucine is an exemplary amino acid which may be incorporated into the formula. Leucine may function in the patch to synthesize sterols, and may also act to regulate blood pressure, energy levels, and hormone secretion. Further, inclusion of leucine in the formula has been found experimentally to reduce appetite levels. While substitution or addition of other amino acids besides leucine may be suitable, it has been found that the use of leucine has resulted in superior results. Adhesive matrix 130 may further comprises glycerin. Glycerin may act as a plasticizer and humectant to preserve the flexibility and formulaic integrity of adhesive matrix 130, and may also provide additional benefits of relieving skin irritation and reducing interference with skin oils when transdermal patch 100 is placed in contact with skin.

Adhesive matrix 130 may also include an adhesive agent and one or more electrolytes. The adhesive agents may include one or more of sodium polyacrylate; polyacrylic acid; carboxymethylcellulose; and povidone. These are exemplary adhesive agents; others may be substituted or supplemented. Preferred electrolytes may include one or more of the following: potassium (as potassium gluconate); calcium (as calcium lactate); magnesium (as magnesium chloride); chloride (as magnesium chloride or sodium chloride); phosphorus (as monosodium phosphate monobasic); and sodium (via the sodium chloride or monosodium monobasic). Yet further, the adhesive matrix may further include acrylases copolymer, as a solvent-based adhesive.

Alternative embodiments may include a child-suitable version having lower doses of active and non-active ingredients. Some embodiments may implement waterproofed elements, versions which include higher levels of amino acids, trademarked versions with logos, etc.

Figure 2:
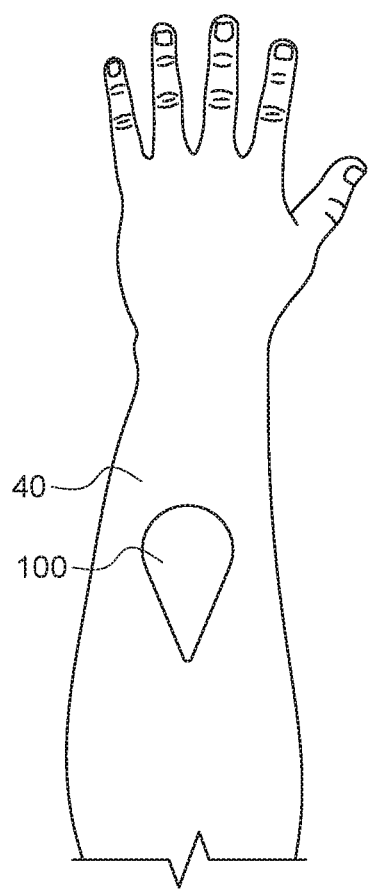
FIG. 2 is a perspective view of the transdermal patch of FIG. 1 in an in-use condition when applied to a user's forearm, according to an embodiment of the present disclosure.

FIG. 2 shows the transdermal patch of FIG. 1, according to an embodiment of the present disclosure. As shown, the transdermal patch 100 may be applied directly to the skin of user 40. Here, transdermal patch 100 is applied to the forearm.

Figure 3:
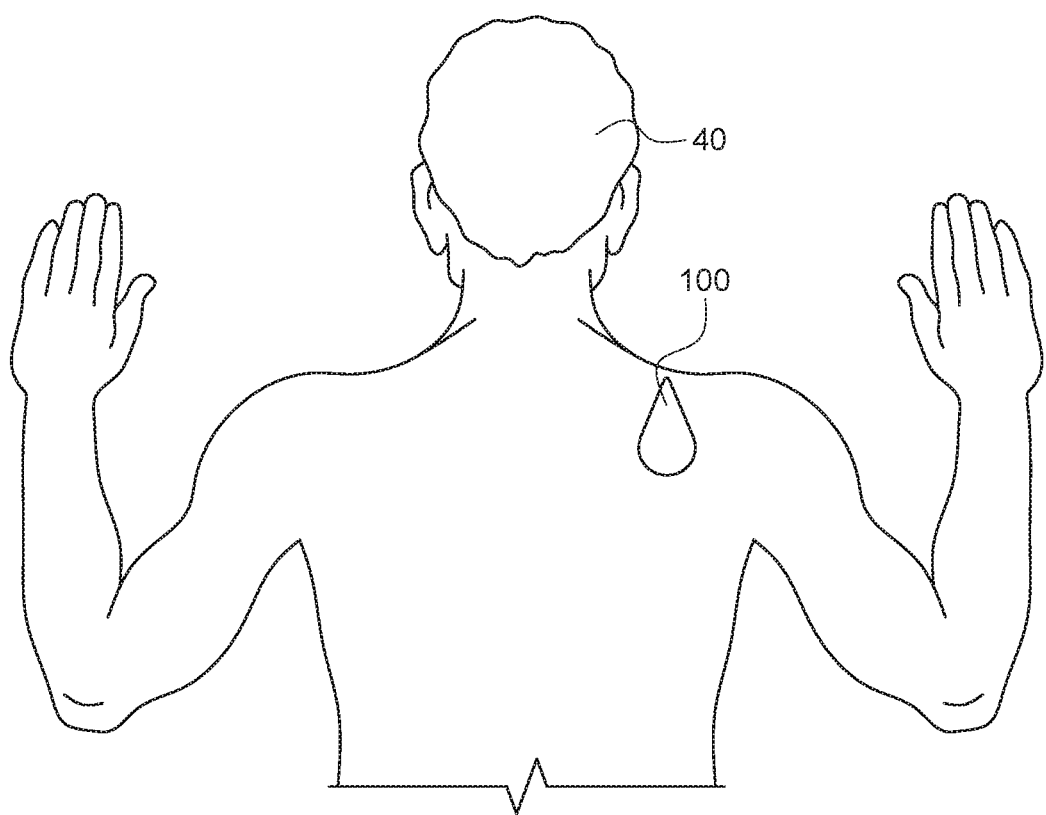
FIG. 3 is a perspective view of the transdermal patch of FIG. 1 in an in-use condition when applied to a user's shoulder, according to an embodiment of the present disclosure.

FIG. 3 shows the transdermal patch of FIG. 1, according to an embodiment of the present disclosure. As shown, the transdermal patch 100 may be applied directly to the skin of user 40. Here, transdermal patch 100 is applied to the shoulder. The shoulder is envisioned as an optimal location for applying transdermal patch 100, as the shoulder is broad and flat enough to easily accommodate larger patches when desired by user 40, and usually lacks excessive body hair which may interfere with the permeation characteristics of transdermal patch 100.

Figure 4:
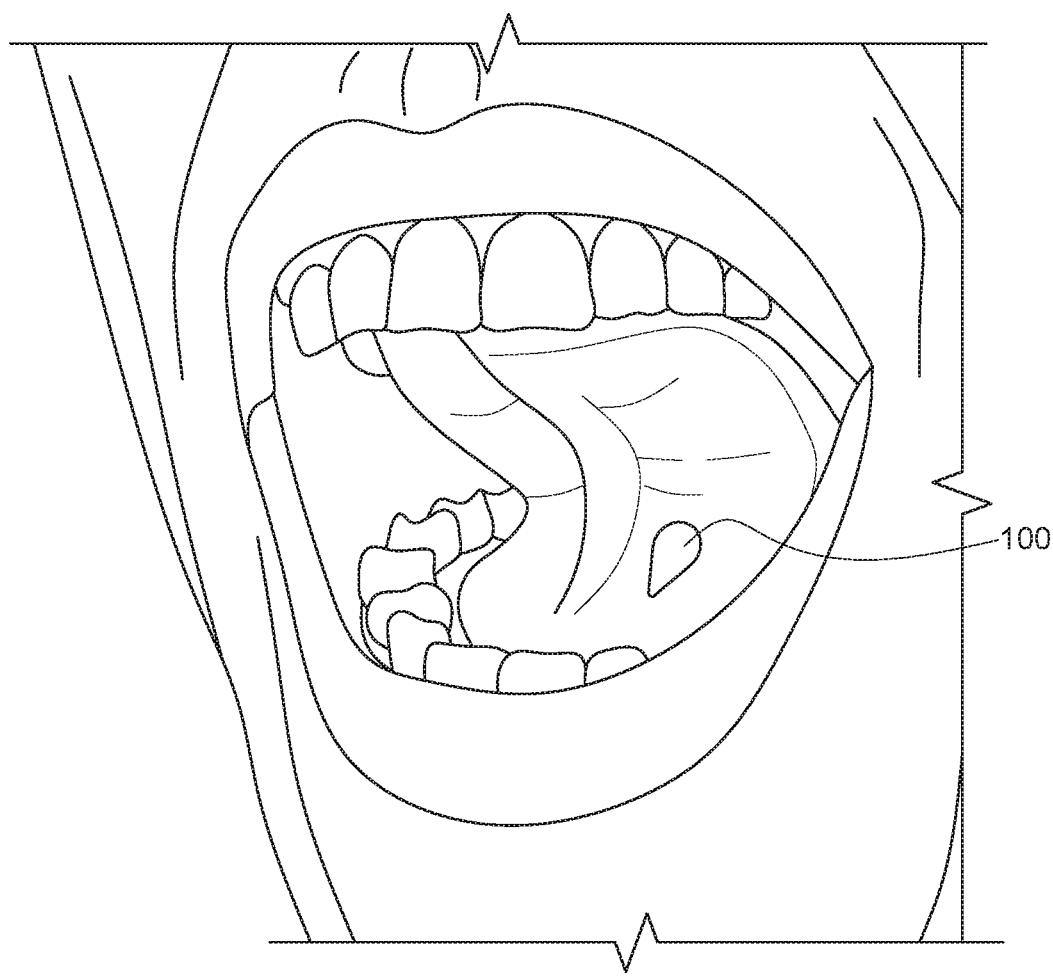
FIG. 4 is a perspective view of the transdermal patch of FIG. 1 when applied to the floor of the mouth as a sublingual patch, according to an embodiment of the present disclosure.

FIG. 4 is a perspective view of the transdermal patch of FIG. 1 when applied to the floor of the mouth as a sublingual patch, according to an embodiment of the present disclosure. As illustrated, transdermal patch 100 may be applied directly to the floor of the mouth of user 40. In some applications, it may be envisioned that transdermal patch 100 may be alternatively applied to the gum, the inside of the cheek, or other locations as preferred by user 40. Like the skin, sublingual mucosa is an advantageous means of delivery of medical ingredients to the bloodstream, and provides similar advantages over traditional methods of ingredient intake (i.e. oral). The same disclosed transdermal patch taught for transdermal permeation may be applied for sublingual use. Some modifications may be envisioned for applications when sublingual use is desired. For example, patches intended for sublingual use may be smaller, and may be constructed of saliva-soluble components in order to dissolve in the mouth, reducing the need to remove the patch after use. Nonetheless, it is envisioned that the same elements and novelties taught herein may make the transdermal patch useful and desirable for sublingual applications as well.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is:

1. A transdermal patch comprising:
    a backer,
    an adhesive for applying the patch to the skin, wherein the adhesive is selected from the group consisting of one or more of sodium polyacrylate, polyacrylic acid, carboxymethyl cellulose, and povidone;
    an adhesive matrix comprising:
        water;
        an electrolyte selected from the group consisting of one or more of potassium, calcium, magnesium, chloride, phosphorus, and sodium;
        a vitamin;
        an amino acid; and
        a permeation enhancer selected from the group consisting of one or more of menthol, dimethyl sulfoxide, and peppermint oil, wherein the permeation enhancer increases the permeation of the one or more electrolytes, vitamins, and amino acids through a subject's skin and into the subject's bloodstream.

2. The transdermal patch according to claim 1, wherein the backer further comprises a polymer that is a waterproof layer.

3. The transdermal patch according to claim 2, wherein the polymer is flexible and suitable for printing a graphic on the backer.

4. The transdermal patch according to claim 1, wherein the adhesive matrix has a smaller coverage area than the backer.

5. The transdermal patch according to claim 1, wherein the patch further comprises a release liner.

6. The transdermal patch according to claim 5, wherein the release liner has a smaller coverage area than the backer.

7. The transdermal patch according to claim 1, wherein the amino acid is leucine.

8. The transdermal patch according to claim 1, wherein the permeation enhancer consists of menthol and dimethyl sulfoxide.

9. The transdermal patch according to claim 1, wherein the adhesive consists of sodium polyacrylate, polyacrylic acid, and carboxymethyl cellulose.

10. The transdermal patch according to claim 1, wherein the adhesive matrix further comprising polysorbate.

11. The transdermal patch according to claim 1, wherein the patch comprises a total mass of between 0.05 ounces and 0.15 ounces.

12. An adhesive matrix for use in a transdermal patch comprising:
   water;
   an electrolyte selected from the group consisting of one or more of potassium, calcium, magnesium, chloride, phosphorus, and sodium;
   a vitamin;
   an amino acid; and
   a permeation enhancer selected from the group consisting of one or more of menthol, dimethyl sulfoxide, and peppermint oil, wherein the permeation enhancer increases the permeation of the one or more electrolytes, vitamins, and amino acids through a subject's skin and into the subject's bloodstream.

13. The adhesive matrix according to claim 12, wherein the electrolyte consists of potassium, calcium, magnesium, chloride, phosphorus, and sodium.

14. The adhesive matrix according to claim 12, wherein the amino acid is leucine.

15. The adhesive matrix according to claim 12, wherein the permeation enhancer consists of menthol, dimethyl sulfoxide, and peppermint oil.

16. The adhesive matrix according to claim 12, further comprising polysorbate.

17. The adhesive matrix according to claim 12, wherein the electrolytes consists of potassium, calcium, magnesium, chloride, phosphorus, and sodium, the amino acid consists of leucine, and the permeation enhancer consists of menthol, dimethyl sulfoxide, and peppermint oil.

18. A method of maintaining hydration of a user comprising the steps of:
   applying a transdermal patch directly to a skin of the user,
   delivering one or more electrolytes, vitamins, and amino acids through the user's skin and into the user's bloodstream, and
   preventing dehydration symptoms selected from the group consisting of one or more of headache, lack of focus, and lethargy,
   wherein the transdermal patch comprises:
   an adhesive matrix comprising:
      water;
      an electrolyte selected from the group consisting of one or more of potassium, calcium, magnesium, chloride, phosphorus, and sodium;
      a vitamin;
      an amino acid; and
      a permeation enhancer selected from the group consisting of one or more of menthol, dimethyl sulfoxide, and peppermint oil, wherein the permeation enhancer increases the permeation of the one or more electrolytes, vitamins, and amino acids through a subject's skin and into the subject's bloodstream.

19. The method of claim 18, wherein the dehydration symptom consists of a headache.

20. The method of claim 18, wherein the dehydration symptom consists of lethargy.

21. The method of claim 18, wherein the dehydration symptom consists of a lack of focus.

* * * * *